United States Patent [19]

Schwarz et al.

[11] Patent Number: 4,988,623
[45] Date of Patent: Jan. 29, 1991

[54] ROTATING BIO-REACTOR CELL CULTURE APPARATUS

[75] Inventors: Ray P. Schwarz, League City; David A. Wolf, Houston, both of Tex.

[73] Assignee: The United States of America as represented by the Administrator of the National Aeronautics and Space Administration, Washington, D.C.

[21] Appl. No.: 213,559

[22] Filed: Jun. 30, 1988

[51] Int. Cl.⁵ .............................................. C12M 3/00
[52] U.S. Cl. ..................... 435/286; 435/284; 435/285; 435/292; 435/311; 435/312; 435/316
[58] Field of Search ........................ 435/284–286, 435/311–313, 315, 316, 292, 294, 240.24, 240.25; 422/209; 210/321.63

[56] References Cited

U.S. PATENT DOCUMENTS

| 3,647,632 | 3/1972 | Johnson et al. | 195/142 |
| 3,676,074 | 7/1972 | Shibayama et al. | 23/259.1 |
| 4,184,916 | 1/1980 | Tolbert et al. | 435/286 |
| 4,244,916 | 1/1981 | Guigan | 422/72 |
| 4,264,739 | 4/1981 | Grabner et al. | 435/241 |
| 4,276,384 | 6/1981 | Mueller | 435/311 |
| 4,310,630 | 1/1982 | Girard et al. | 435/284 |
| 4,343,904 | 8/1982 | Birch et al. | 435/240 |
| 4,535,062 | 8/1985 | Muller | 435/289 |
| 4,537,860 | 8/1985 | Tolbert et al. | 435/240 |
| 4,596,779 | 6/1986 | Ono | 435/286 |
| 4,605,626 | 8/1986 | Beck | 435/291 |
| 4,649,117 | 3/1987 | Famillett | 435/313 |
| 4,649,118 | 3/1987 | Anderson | 435/316 |

FOREIGN PATENT DOCUMENTS 0164888 12/1985 European Pat. Off. ............. 435/286

OTHER PUBLICATIONS

Lewis et al., "Growth and Maintenance of Anchorage Dependent Cells in Zero Headspace Bioreactor Systems Designed for Microgravity", Spacebound Proceedings Abstract, (5/6/87).
Lewis et al., "Growth and Maintenance of Anchorage Dependent Cells in Zero Headspace Bioreactor Systems Designed for Microgravity", Spacebound Proceeding Paper (9/14/87).
"The Large-Scale Cultivation of Mammalian Cells," Scientific American, Jan. 1983, vol. 248, #1, pp. 36–43, authors Feder and William R. Tolbert.
"The Clinostat—A Tool for Analysing the Influence of Acceleration on Solid-Liquid Systems," Instutde for Aerospace Medicine, Cologne, Germany, Proceeding of a workshop on Space Biology, Cologne, Germany, Mar. 9–11, 1983, pp. 97–101, author, W. Briegled.
"Particle Orbits in a Rotating Liquid," Space Science Laboratory, NASA Marshall Space Flight Center, Huntsville, Ala. 35812, and Gyln O. Roberts, Roberts Associates, Inc., Vienna Vir., 222180, authors—William W. Fowlis & Dale M. Kornfeld.
"Gravisensitivity of the Acellular Slime Mold Physarum Polycephalum Demonstrated on the Fast-Roating Clinostat," European Journal of Cell Biology, pp. 44–50, Dec. 30, 1985, authors—Ingrid Block and Wolfgang Briegleb.

Primary Examiner—Christine Nucker
Assistant Examiner—William H. Beisner
Attorney, Agent, or Firm—Russell E. Schlorff; John R. Manning; Edward K. Fein

[57] ABSTRACT

A bio-reactor system wherein a tubular housing contains an internal circularly disposed set of blade members and a central tubular filter all mounted for rotation about a common horizontal axis and each having independent rotational support and rotational drive mechanisms. The housing, blade members and filter preferably are driven at a constant slow speed for placing a fluid culture medium with discrete microbeads and cell cultures in a discrete spatial suspension in the housing. Replacement fluid medium is symmetrically input and fluid medium is symmetrically output from the housing where the input and the output are apart of a loop providing a constant or intermittent flow of fluid medium in a closed loop.

16 Claims, 2 Drawing Sheets

ROTATING BIO-REACTOR CELL CULTURE APPARATUS

ORIGIN OF THE INVENTION

The invention described herein was made in the performance of work under a NASA contract and is subject to provisions of Section 305 of the National Aeronautics and Space Act of 1958, Public Law 85-568 (72 Stat. 435; 42 U.S.C. 2457).

RELATED APPLICATIONS

This application has subject matter related to the subject matter disclosed in the U.S. patent applications Ser. No. 087,358, filed Aug. 20, 1987, now U.S. Pat. No. 4,839,046 (MSC-20929-1) and Ser. No. 07/213558, filed June 30, 1988 (MSC-21294-1).

1. Field of the Invention

The present invention relates to an improved bio-reactor vessel system useful for carrying out cell production of mammalian cells in an earth based microgravity environment.

2. Background of the Invention

Bacterial cell culture processes have been developed for the growth of single cell bacteria, yeast and molds which are encased with a tough cell wall. Mammalian cell culture, however, is much more complex because such cells are more delicate and have a more complex nutrient requirement for development. Large scale culture of bacterial type cells is highly developed and such culture techniques are less demanding and are not as difficult to cultivate as mammalian cells. Bacterial cells can be grown in large volumes of liquid medium and can be vigorously agitated without any significant damage. Mammalian cells, on the other hand, cannot withstand excessive turbulent action without damage to the cells and must be provided with a complex nutrient medium to support growth.

In addition, mammalian cells have other special requirements such that most animal cells must attach themselves to some surface to duplicate. On a small scale, mammalian cells have been grown in containers with small microwells to provide surface anchors for the cells. However, the cell culture for mammalian cells in the containers with microwells generally does not provide sufficient surface area to grow mammalian cells on a large scale basis. To provide greater surface areas, microcarrier beads have been developed for providing surface areas for the cultured cells to attach. Microcarrier beads with attached culture cells require agitation in a bio-reactor vessel to provide suspension of the cells in fresh nutrients. To obtain agitation, such bio-reactor vessels have used internal propellers or movable mechanical agitation devices which are motor driven so that the moving parts within a vessel cause agitation in the fluid medium for the suspension of mammalian cells carried on microcarrier beads.

Bio-reactor vessels with internal moving parts may damage mammalian cells and also subject the cells to high fluid shearing stresses. If the beads collide with one other, the cells can be damaged. One way to reduce the effect of collision of the beads during agitation of the medium in a bio-reactor, is to reduce the density of microcarriers in the present bio-reactors which in turn reduces the cell production.

In summary, bio-reactors used to culture mammalian cells typically utilize internal mechanical parts, air, or fluid movement as a lift mechanism to achieve particle suspension. Such mechanisms induce damage to growing cells or tissues either directly or indirectly by fluid shear.

PRIOR ART

Prior art which is known to applicant include the following:

Paper entitled, "The Clinostat—A Tool For Analyzing The Influence Of Acceleration On Solid-Liquid Systems" by W. Briegleb, published by the proceedings of a workshop on Space Biology, Cologne Germany, on Mar. 11, 1983 (ESASP-206, May 1983). In this paper, clinostat principals are described and analyzed relative to gravity affects. Some clinostat experiments are described including experiments where cultures are grown within cylinders which are rotated about a horizontal axis.

Paper entitled, "Particle Orbits In A Rotating Liquid", by William W. Fowlis and Dale M. Kornfeld, a Nasa white paper planned for publication. The Nasa paper discloses use of microspheres up to 3 micrometers in diameter in a rotating reactor cylinder where the cylinder is rotated about a horizontal axis to keep the particles in suspension. The rotation of the reactor cylinder maintains the particles in suspension without agitation to cause particle collision" which would result in flocculation.

U.S. Pat. No. 3,676,074 relates to an apparatus for treating organic waste where a cylinder is rotated about a stationary pipe which has a central air input for supplying an air input to the waste material.

U.S. Pat. No. 4,537,860 which relates to a static or stationary system for cell culture of animal cells where the cells in the vessel are supplied with a nutrient 21 which passes through a porous tube 19 into the matrix (with cells) and that exits through passages 24 and 25. Oxygen is passed through a permeable membrane 25.

U.S. Pat. No. 4,310,630 relates to a stationary or static cell culture growth device. In the '630 patent, the patentee proposes to have a rotating cylinder about a horizontal axis which is rotatable between 5 and 20 RPM. Included within the vessel is a matrix of tubular elements 11 for providing increased surface area for growth of cells. Not all of the elements 11 are covered with nutrient and the gas is supplied through one inlet and exited through an outlet.

In U.S. Pat. No. 4,605,626, an electrode assembly 16 is rotated about a vertical axis and inert gas is passed through a gas sparger 26 for dispersal as bubbles into a bacteria solution 14. The shaft rotates and agitates while the chamber remains static.

U.S. Pat. No. 4,264,739 relates to a sparger for a mass cell culture system which is comprised of an elongated tube having a plurality of ports.

U.S. Pat. No. 4,343,904 relates to growth of animal cells and a vertical cylindrical vessel having spaced apart plates on an axial shaft. An external pumping loop is provided for circulating the contents of the vessel from the bottom to the top of the vessel. Cell growth is carried out by substantially filling the vessel with cells and growth medium and allowing the cells to settle onto disk surfaces and rotating the shaft while circulating the vessel contents from the bottom to the top for mixing.

U.S. Pat. No. 4,649,117 discloses an air lift bio-reactor for maintaining cells in suspension and includes a centrally located gas inlet means at the lower end of the mixing chamber, a conical side wall in the growth chamber and introducing an oxygen containing gas to bubble up through the cells and liquid medium to carry the cells and liquid medium upward from the mixing chamber to the growth chamber and so that the cells and liquid medium flow downwardly along the conical side wall to replace the cells and liquid medium being carried upwards in the mixing chamber. The system is for agitating the cells while minimizing shear forces.

A paper entitled, "The Large Scale Cultivation of Mammalian Cells", by Joseph Feder and William R. Tolbert, published in the Scientific American Magazine, January 1983, Vol. 248, No. 1. pps. 36–43. In this paper, agitation of the cells is described as required to keep the cells suspended in the medium and describes a turbine agitator, a marine propeller agitator, and a vibro mixer for mixing. The paper also describes a perfusion reactor in which an agitation is provided by four slowly rotating flexible sheets of monofilament nylon which are rotated about a vertical axis while the medium in the main vessel is continuously pumped to the satellite filter vessel. The filter retains the cells which are pumped along with the remainder medium back into the vessel for further proliferation.

A paper entitled, "Gravinsensitivity Of The Acellular, Slime, Mold, Physarum, Polycephalum Demonstrated On The Fast Rotating Clinostat", by Ingrid Block and Wolfgang Brigleb, published in the European Journal of Cell Biology 41, pps. 44–50, 1986. This paper describes rotation of a culture vessel about a horizontal axis for the stimulation of weightlessness. The paper is a study relative to the gravity influences in the control systems of cells.

The U.S. Pat. No. 3,647,632 shows an apparatus for handling cells in which a centrally located filter is rotated by an external magnetic drive. Fluid and gas are supplied to the mixture for cell growth and fluid is withdrawn from the center of the rotating filter. Samples may be taken of the fluid by an external device and an annularly heating bath is provided for maintaining the temperature of the culture medium. The device does not show the complete enclosure to be filled with fluid. In the Johnson patent the device is rotated about a vertical axis.

U.S. Pat. No. 4,244,916 illustrates a centrifuge rotated about a vertical axis in which a sample is placed within the annular filter and centrifuged outwardly into peripheral cells containing a re-agent.

In U.S. Pat. No. 4,596,779 a culture vessel has an agitator arranged to orbit about an upright axis. The culture system utilizes microcarrier beads and suspension of the beads in the solution as well as a continuous perfusion culture system which involves removing the media from the culture vessel and supplying fresh medium. In the system agitator 51 orbits but does not rotate. A filter 78 performs functions of agitating and exchange of media between the vessels without stopping movement of the agitator.

U.S. Pat. No. 4,649,118 discloses and relates to the handling of cell cultures for continuously removing expended medium to facilitate cell growth and concentration. The patent illustrates a culture vessel containing a quantity of culture medium with a filter head which is moved in a swinging fashion through the support member through the fluid to create shearing forces about the periphery of the filter 48 to prevent undesirable buildup and clogging of cells and to accomplish such motion a magnetic motor drive is provided.

The U.S. Pat. No. 4,535,062 discloses a fermenting device with a rotary turbine 14 where backflushing of fluid is provided through diaphragm filters and aeriation is provided through an aeriating pipe and a distributing member. The filter is not rotated.

U.S. Pat. No. 4,276,384 discloses a fermenter for growing micro-organisms and illustrates a rotary means which are rotatable about a vertical axis.

SUMMARY OF THE PRESENT INVENTION

The bio-reactor system of the present invention is for growing mammalian cells where the cell culture is unfettered by sedimentation collision of cells, or adverse shear forces and where the system has optional operating characteristics. The bio-reactor system of the present invention utilizes the clinostat principal that a fluid medium rotated about an approximately horizontal axis suspends discrete particles in the fluid so that the discrete particles are suspended in discrete spatial locations. The outer wall containing the fluid medium may be rotated to minimize adverse boundary layer shear forces induced by velocity gradients between the wall and the fluid medium.

The bio-reactor apparatus basically includes an outer tubular enclosure with end caps to define a cell culture enclosure. The outer tubular enclosure is rotatively supported on input and output shaft members and rotatively driven by an independent drive means. Coaxially disposed within the tubular enclosure is a central tubular filter member which is rotatively supported on the input shaft and coupled to the output shaft. The output shaft is rotatively driven by an independent drive means.

The annular space between the inner and outer tubular members defines a cell culture chamber. Two blade members positioned about the horizontal axis and extend lengthwise of the cell culture chamber. The blade members have radial arms at one end which are rotatively supported on the output shaft and radial arms at the other end which are coupled to the input shaft. The input shaft is rotatively driven by an independent drive means.

The independent drive means normally drives the inner and outer tubular members and the blade members at the same angularly rate and direction so that no relative motion occurs between these members. Thus, a clinostat motion of particles in the fluid within the cell culture chamber can be obtained with the structure.

The bio-reactor has a fluid input at a stationary input location for inputting fresh fluid medium to the cell culture chamber. The fluid medium passes through a rotational coupling at the stationary input location to a passageway in the input shaft and from the input shaft the fluid passes through split distribution passageway system in the outer tubular member so as to be input to the cell culture chamber at spaced apart locations which are circumferentially located about the input and output shafts at the inner end surfaces of the cell culture chamber. Fluid motion of fresh fluid medium within the cell culture chamber is from the periphery of the input and output shafts at the end surfaces and in a somewhat toroidal motion in moving radially outward toward the inner wall of the outer tubular member and then moving from both end surfaces toward the midpoint transverse plane of the cell culture chamber and then moving radially inward to pass through openings disposed along the inner tubular member. The inner tubular member receives spent fluid medium and has an outlet passageway which is coupled through the output shaft and a rotational coupling to exit from a stationary outlet location.

In the development of cell growth in the bio-reactor, the cell culture chamber is filled with fluid medium containing nutrients, microcarrier beads and the cells for growth. The medium completely fills the cell culture vessel so that there are no air pockets or bubbles (sometimes called "zero head-space"). The inner member, the outer member and the blade members are simultaneously rotated to obtain clinostat operation in suspending the beads in a spatial positions within the medium. Fresh fluid medium is input either intermittently or continuously through the input shaft with fresh nutrients containing oxygen for cell growth while the bio-reactor is rotated under proper incubation conditions for the cell growth. The beads are prevented from exiting the cells culture chamber by an annular filter cloth on the inner member.

Should the filter cloth or inner member tend to clot, the speed of the inner member can be increased to spin free any clots on the cloth. Should agitation be desirable, the speed of the blade members can be increased to produce agitation. Alternatively, if the rotation of the outer member is stopped, for example, to withdraw a sample then the blade members can be rotated to maintain a suspension of the cell cultures.

Tissue culture on Earth has limitations imposed by the presence of gravity. By nature, the growing cell systems have varying densities, usually greater than a culture media, and therefore sedimentation occurs within conventional culture vessels. Impellers or air lift mechanisms are utilized to maintain the homogeneous distribution of cells, nutrients, and waste products required to maintain a healthy culture. However, such mechanisms disrupt natural cell processes and in many cases damage or kill delicate mammalian cells. The present invention allows cultures to remain evenly suspended, in three dimensions, without introducing damaging forces. The living cells are suspended inside a rotating cylindrical vessel about an approximate horizontal rotational axis where the vessel is completely filled with culture media and beads. Delicate cells are cultured at very high densities and unique associations of cells into tissue-like groups. In some cases this rotating, or clinostatic, culture technique provides a practical method to culture sufficient numbers of delicate cells for further studies.

The unique design of this cell and tissue culture device was initially driven by three requirements imposed by its intended use for three dimensional culture of living cells and tissues in space by NASA. There were (1) compatability with microgravity and (2) simulation of microgravity in one G, and (3) to allow precision control and sampling of the culture environment. The vessels are designed to approximate the extremely quiescent low shear environment obtainable in space where it would be unnecessary for a lifting mechanism to oppose particle sedimentation. This gentle culture environment was hypothesized to allow cells to achieve and maintain a three dimensional orientation, according to cellular derived forces, and thus form higher order tissue structures. The rotating wall culture vessels, with associated features herein disclosed and developed for these purposes, were found to allow living cell cultures which exhibited the hypothesized features. It is observed that the rotating fluid effectively counters sedimentation and that the rotating wall effectively reduces adverse fluid velocity gradients through the boundry layer at the vessel wall. The combined effects allowed cultures to be maintained in large three dimensional orientation without introducing disruptive shear forces which would limit the viability of delicate cell types (particularly mammalian) and would limit the assembly of cells into higher order structures. It is observed in the case of attachment dependent cultures maintained on microcarrier beads that the hundreds or thousands of beads participate in the formation of large high order structures bound by cell bridging. Along the center axis of the vessel, is placed the media outlet spin filter which allows cell free culture media to be circulated for reconditioning and gas exchange external to the vessel. This external perfusion loop allows for introducing nutrients, removing waste products, and exchange of dissolved respiratory gases. By measuring inlet and outlet concentrations of metabolic components, cell numbers, and perfusion flow rate the "Fick" principle may be utilized to calculate the consumption or production (by the living cells) of metabolites (e.g. oxygen or glucose consumption). Factors such as hormones, growth factors, and immune modulators may be introduced without disruption of the culture. Real time measurement of conditions within the vessel may be obtained (on the effluent media) for research data and precise feedback control of vessel conditions. It was apparent to scientists utilizing this instrumentation that it offered significant advantages for earth based cell and tissue culture research in terms of efficient utilization of vessel volume, logistics of sampling and measurement, and unique culture capabilities (particularly for attachment dependent microcarrier cultures). Additional benefit is derived from the efficient utilization of the vessel volume for culture allowing improved logistics where cell or cell product production is concerned. Soluble products may be extracted from the external perfusion loop as the culture progresses.

A vane may be introduced and rotated at nearly the same speed as the wall and fluid in order to extend the operating range by giving an extra boost to rapidly falling particles so they get over the top and follow the general streamline direction. Differential vane rotation rates (from the wall), discs, or impellers may be utilized to induce additional mixing or shear if this is desirable.

The present invention is some respects an improvement over the horizontally rotating cell culture system disclosed in pending application Ser. No. 07/213,558 filed June 30, 1988, (MSC 21294-1), and such application is hereby incorporated by reference. The present invention in addition to the improved cell growth of said application permits continuous perfusion.

DESCRIPTION OF THE PREFERRED EMBODIMENT

Figure 1:
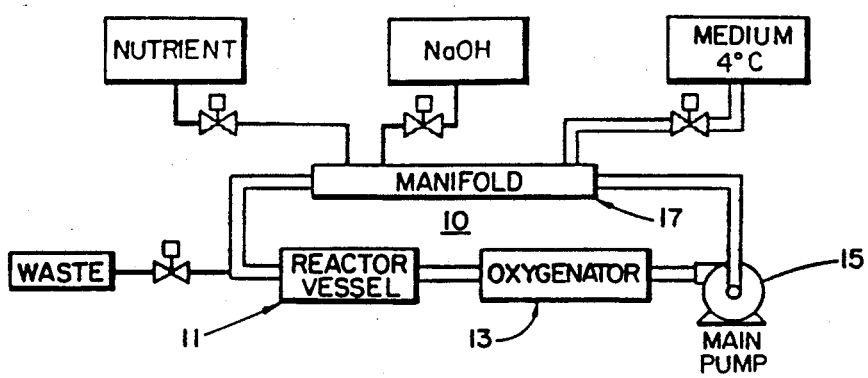
FIG. 1 schematically illustrates a system loop utilizing the present invention.

Referring now to FIG. 1, in the overall system illustrated, a main fluid flow loop 10 for growing mammilian cells includes a rotating cell culture reactor vessel 11, an oxygenator 13, a main pump 15 and a supply manifold 17 for the selective input of nutrients, acids, bases, or buffers, such as, sodium hydroxide or fresh medium. The main pump 15 provides fresh fluid medium to the oxygenator 13 where the fluid medium is oxygenated and passed through the cell culture reactor vessel 11. The return spent fluid medium from the cell culture reactor is returned to the manifold 17 where it receives a fresh charge of nutrients, sodium hydroxide or liquid medium, as necessary, before recycling by the pump 15 through the oxygenator 13 and to the cell culture vessel 11. Thus, a continuous loop system is provided for the cell growth in the cell culture reactor vessel.

In the system 10, the culture fluid medium is circulated through the living cell culture in the vessel 11 and around an external life support loop, as shown in the FIG. 1. In this external loop, adjustments are made in response to chemical sensors (not shown) which maintain constant conditions within the cell culture vessel 11. PH is corrected by controlling carbon dioxide pressures and introducing acids or bases. Oxygen, nitrogen, and carbon dioxide dissolved gas concentrations are maintained by a closed loop gas exchange system (not shown) in order to support cell respiration. The closed loop adds oxygen and removes carbon dioxide from a circulating gas capacitance. In this way the minimum amount of stored gases may be taken into space if the device is utilized on a space station or other space vehicles.

Figure 2:
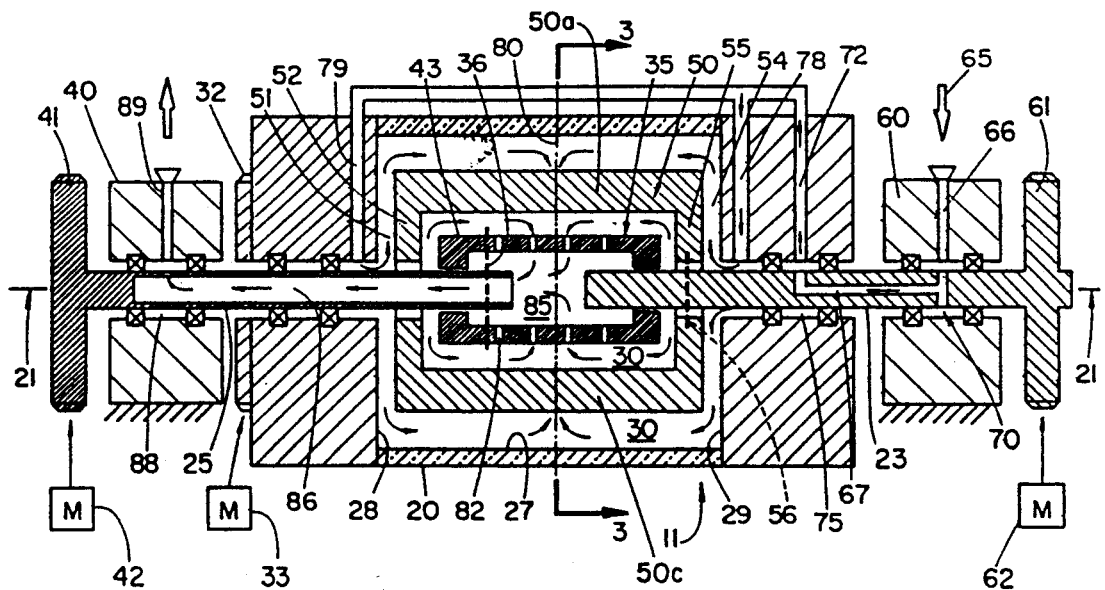
FIG 2 schematically illustrates the present invention in vertical cross section.
Figure 3:
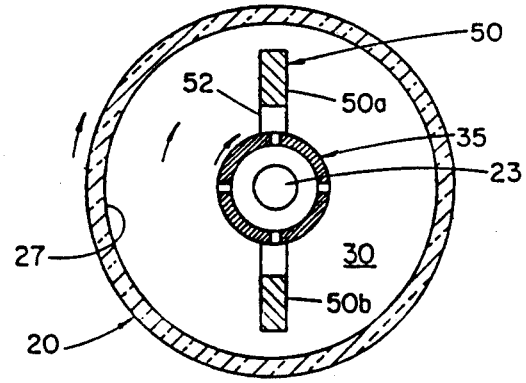
FIG. 3 is a view in cross section along line 3—3 of FIG. 2.

FIGS. 2 and 3 schematically illustrate the general details of a rotatable bio-reactor or cell culture reactor vessel 11 illustrating the present invention. In FIGS. 2 and 3, an outer tubular housing 20 is rotatably supported for rotation about a horizontal central axis 21 and about an input shaft 23 and an output shaft 25 which are aligned with the central axis. The outer tubular housing 20 has a cylindrically shaped interior wall 27 and transverse end walls 28, 29 which generally define a cylindrically shaped, elongated cell culture chamber 30. A spur gear 32 is attached to one end of the housing 20 and is driven by a motor 33 to rotate the housing about its central horizontal axis 21.

Coaxially disposed about the central axis 21 is a tubular inner filter assembly or member 35 which is rotatably mounted on the input shaft 23 and is coupled (as shown by the dashed line 36) to the output shaft 25. The output shaft 25, in turn, is rotatably supported in a stationary housing 40 and the output shaft has an externally located spur gear 41 which is connected to a drive means 42 for rotating the output shaft 25 and the inner filter assembly 35 independently of the outer housing 20. The annular space 30 between the inner filter assembly 35 and the interior wall 27 of the outer housing member 20 define the annular cell culture chamber 30 located about the horizontal axis 21. Intermediate of the outer wall 43 of inner filter assembly 35 and the inner wall 27 of the outer member 20 is a blade member system 50 which includes two lengthwise extending blade members 50a and 50b which are equiangularly spaced from one another about the central axis 21. Each of the blade members 50a and 50b at one longitudinal end have a radial arm 52 which is rotatably supported on the output shaft 25 and at an opposite longitudinal end 54 have a radial arm 55 which is coupled to the input shaft 23 (shown by the dashed line 56). The input shaft 23, in turn, is rotatably mounted in a stationary housing 60 and the input shaft has a spur gear 61 which is driven by an independent drive mechanism 62 for rotation of the blade members 50 independent of the inner filter assembly 35 and rotation independent of the rotation of the outer member 20.

As shown in FIG. 3, the angular rotation of the three sub-assemblies 20, 35 and 50, i.e. the inner filter member 35, the outer housing member 20 and the intermediate blade member 50, can be at the same angular rate and in the same direction about a horizontal rotational axis so that there is no relative movement between the three sub-assemblies. This condition of operation obtains a clinostat suspension of microcarrier beads in a fluid medium within the cell culture chamber without turbulence.

The rotation of the filter can be started and stopped which will cause the turbulence on the surface of the filter and keep the surface clean. The blade members or vanes 50a and 50b assist cell cultures as they grow to maintain spatial positions in the rotating fluid medium. This is particularly helpful for higher density culture particles such as bone cells. By rotating the fluid and the outer wall, the velocity gradient at the wall boundary layer is nearly eliminated.

Referring again to FIG. 2, fluid medium containing fresh nutrients and gases is input, as shown by an arrow 65, to a passageway 66 in the stationary housing 60 and connects to a longitudinal passageway 67 in the input shaft 23 by virtue of a sealed rotative coupling 70. The passageway 67 in the input shaft 23 couples to a radial supply passageway 72 in an end cap of the outer member 20 by virtue of a sealed rotative coupling 75. The radial supply passageway 72, in turn, connects to spaced apart radially directed input passages 78, 79 in the outer housing 20 member where the input passages 78, 79 are located at opposite ends of the cell culture chamber 30. As shown by the arrows, when fluid is input at both ends of the cell culture chamber 30, the fluid moves radially outward toward the inner wall 27 of the outer housing member and then moves longitudinally in a horizontal direction toward a midpoint plane generally indicated by a vertically dashed line 80 and then moves radially inwardly toward the outer wall 43 of inner filter assembly 35. Thus the fluid in the chamber 30 has a generally toroidal type of motion in radial planes on either side of the midpoint transverse plane 80 of the outer member 20. The inner filter assembly 35 has openings 82 along its length for exit passage of fluid and, while not illustrated in FIG. 2, there is a lengthwise extending filter cloth located across the openings 82 which prevents microcarrier bead members in the chamber 30 from exiting through the open-ings 82. Spent fluid in the cell culture chamber 30 thus is passed to the interior 85 of the inner filter assembly 35 and exits via a passageway 86 in the output shaft 25 to a rotative coupling output 88 in the stationary housing 40 and to a passageway 89 to the return of the loop passageway for recharging.

Figure 4:
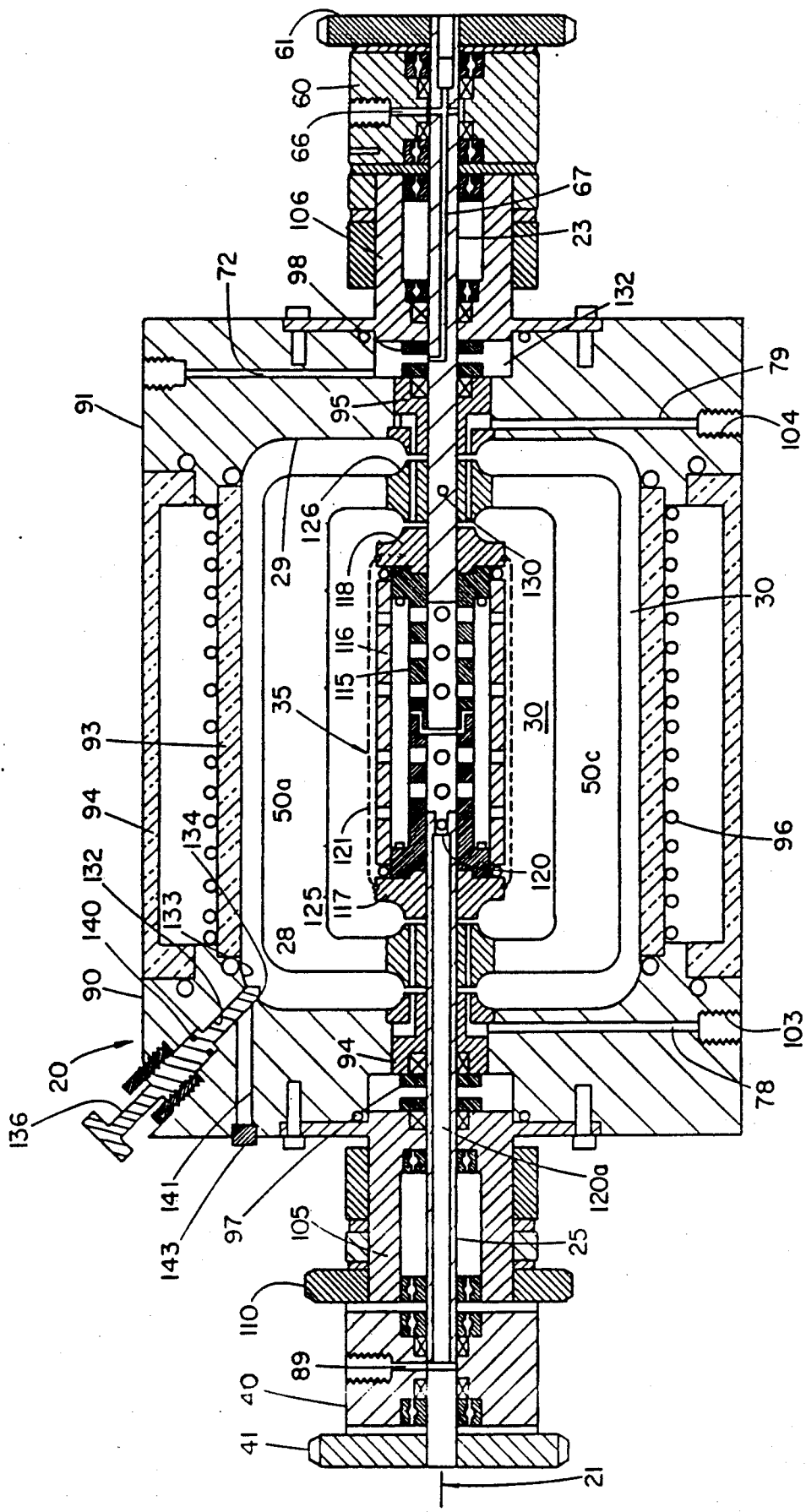
FIG. 4 is a view in vertical cross section similar to FIG. 2 but illustrating more detail.

Referring now to FIG. 4, a detailed drawing of the bio-reactor of the present invention in a preferred form is illustrated. The outer housing 20 includes left and right hand cylindrically shaped transverse end cap members 90, 91 which have facing end surfaces 28, 29 arranged to receive an inner cylindrical tubular glass member 93 and an outer tubular glass member 94. Suitable pressure seals are provided. Between the inner and outer tubular members 93, 94 is an annular wire heater 96 which is utilized for obtaining the proper incubation temperatures for cell growth. The left and right hand end cap members 90, 91 have inner curved surfaces adjoining the end surfaces 28, 29 for promoting smoother flow of the fluid within the chamber 30. The end cap members 90, 91 have central fluid transfer journal members 94, 95 which are rotatably received respectively on an input shaft and an output shaft. Each housing journal member 94, 95 has a flange to seat in a recessed counter bore in an end cap member and is attached by a lock washer and ring 97, 98 against longitudinal motion relative to a shaft. Each journal member 94, 95 has an intermediate annular recess which is connected to longitudinally extending, circumferentially arranged passages. Each annular recess in a journal housing is coupled by a radially disposed passage in an end cap member 90 or 91 to an input coupling 103, 104. Fluid in a radial passage 78 or 79 flows through an annular recess and the longitudinal passages in a journal member 94 or 95 to permit access fluid through a journal member to each end of the journal where the access is circumferential about a shaft.

Attached to the end cap members 90 and 91 are tubular bearing housings 105, 106 containing ball bearings which rotatively support the housing member 20 on the input and output shafts 23 and 25. On the left hand bearing housing 105 has an attached sprocket gear 110 for providing a rotative drive for the housing member 20 in a rotative direction about the input and output shafts 23, 25 and the central axis 21. The housings 105, 106 also provide for electrical take out of the heater wire 96 and any other sensor.

The inner filter assembly 35 includes inner and outer tubular members 115, 116 having perforations or openings along their lengths and end cap members 117, 118. The inner tubular member 115 is constructed in two pieces with an interlocking centrally located coupling section and each piece attached to an end cap 117 or 118. The outer tubular member 116 is mounted between the end caps 117 and 118.

The end cap members 117, 118 are respectively rotatably supported on the input shaft 23 and the output shaft 25. The inner member 115 is rotatively attached to the output shaft 25 by a pin and an interfitting groove 120. A polyester cloth 121 with a ten micron weave is disposed over the outer surface of the outer member 116 and attached thereto by O-rings at either end. Because the inner member 115 is attached by a coupling pin to a slot in the output drive shaft 25, the output drive shaft 25 can rotate the inner member 115. The inner member 115 is coupled by the end caps 117 and 118 which support the outer member 116. The output drive shaft 25 is extended through bearings in a left hand stationary housing 40 and is coupled to a sprocket gear 41.

As illustrated, the output shaft 25 has a tubular bore 120a which extends from a port or passageway 89 in the stationary housing 40 located between seals to the inner member 115 so that a flow of fluid can be exited from the inner member 115 through the stationary housing 40.

Between the end caps 117 and 118 for the inner member 35 and the journals 94, 95 in the outer, member 20, are hubs 125, 126 for the blade members 50a and 50b. The hub 126 on the input shaft 23 is coupled to the input shaft 23 by a pin 130 so that the hub 126 rotates with the input shaft 23. Each hub 125, 126 has axially extending passageways for the transmittal of fluid medium through a hub. The input shaft 23 extends through bearings in the right hand stationary bearing housing for rotatable support of the input shaft 23. A longitudinal passageway 67 extends through the input shaft 23 to a location intermediate of retaining washers and rings which are disposed in an annular recess 132 between face place and the housing. A radial passageway 72 in the end cap member 91 permits fluid in the recess to exit from the end cap member 91. While not shown, the passageway 72 connects through piping and a Y joint to each of the passages 78 and 79. It will be appreciated that there is a substantial symmetry of construction with respect to the vertical plane defined by line 3—3 of FIG. 3.

A sample port is shown in FIG. 4, where a first bore 132 extending along a first axis intersects a corner 133 of the chamber 30 and forms a restricted opening 134. The bore 132 has a counterbore and a threaded ring at one end to threadedly receive a cylindrical valve member 136. The valve member 136 has a complimentarily formed tip to engage the opening 134 and protrude slightly into the interior of the chamber 30. An O-ring 140 on the valve member 136 provides a seal. A second bore 141 along a second axis intersects the bore 132 at a location between the O-ring 140 and the opening 134. An elastomer or plastic stopper 143 closes the bore 141 and can be entered with a hypodermic syringe for removing a sample. To remove a sample, the valve member 136 is backed off to access the opening 134 and the bore 141. A syringe can then be used to extract a sample and the opening 134 can be reclosed. No outside contamination reaches the interior of the vessel.

In operation, fluid is input to the passageway 66 to the shaft passageway 67 and thence to the end member passageways 78 and 79 via the passageway 72. When the fluid enters the chamber 30 via the longitudinal passages in the journals 95, 94 the fluid impinges on an end surface of the blade journals 125, 126 and is dispersed radially as well as axially through the passageways in the journals 125, 126. Fluid passing through the journals 125, 126 impinges on the end caps 117, 118 and is dispersed radially. The flow of entry fluid is thus radially outward away from the central axis 21 and flows in a toroidal fashion from each end to exit through the filter 121 and openings in filter assembly 35 to exit via the passageways 120 and 89. By controlling the rotational speed and direction of rotation of the assemblies 20, 50 and 35 any desired type of fluid action can be obtained. Of major importance, however, is the fact that a clinostat operation can be obtained together with a continuous supply of fresh medium and oxygen.

Microgravity as utilized in the present invention provides a unique environment for growing living cellular systems because the direction of the gravity vector is controlled by rotating a zero head-space culture vessel. This "randomization" of gravity allows ground-based cell growth which to some degree simulate microgravity tissue culture in space. The cultures have a 3-dimensional freedom for cell and substrate interactions. The culture environment is extremely quiescent and free of the high fluid velocity gradients and sedimentation effects found in conventional vertical axis culture systems. These unique properties allow "tissue-like" aggregations of growing cells to be studied under precisely controlled conditions. Very high growth rates and viability are observed for delicate cell types cultured in this simulated microgravity environment.

In use, the apparatus is sterilized, for example, with ethylene oxide and placed in an incubator. The vessel with an internal volume of 500 ml was charged with microcarrier medium containing 100 units of Penicillin and 100 micrograms of Streptomycin pu ml and 10% Fetal Bovine Serum (FBS). To that was added 5 mg of Cytodex 3 microcarriers per ml of vessel volume. The system was stabilized in a $CO_2$ environment to 37° C. and 38 $mmHgCo_2$ pressure. Following stabilization, the system was inoculated with Baby Hamster Kidney (BHK) cells at a density of about 6 BHK cells per bead. At 27 hours, the system was perfused with 1000 ml of medium containing 10% FBS, no increase in cell members was noted after the perfusion but some confluent beads were observed. At 52 hours, a second perfusion was performed with 500 ml of medium containing 10% FBS and the pump rate was increased from 5 to 7 ml per minute. At 79 hours a third perfusion of 1650 ml was made and at 121 hours a fourth perfusion was made. Two additional perfusions were carried out at 149 hours and at 173 hours with 1% FBS. At the termination of the experiment, the system was vane stirred with the outer housing stationary for 6 hours at 15 RPM. No cell damage values were obtained.

It will be apparent to those skilled in the art that various changes may be made in the invention without departing from the spirit and scope thereof and therefore the invention is not limited by that which is enclosed in the drawings and specifications but only as indicated in the appended claims.

We claim:

1. A bio-reactor system including
   an outer first tubular member having closed ends for defining an enclosed cell culture vessel, said tubular member having a horizontally extending, longitude, central axis;
   first means for rotating said first tubular member about said central axis;
   a central second tubular member mounted within said first tubular member for rotation about said central axis, said second tubular member and said first tubular member defining an annular cell culture chamber;
   second means for rotating said second tubular member about said central axis;
   an intermediate blade means mounted in said annular cell culture chamber for rotation about said central axis;
   third means for rotating said blade means about said central axis; where said first, second and third means for rotating are capable of providing independent rotation with respect to one another; and
   first passage means for connecting an input fluid to said cell culture chamber and second passage means for connecting said cell culture chamber and said second tubular member for output of fluid from said cell culture chamber whereby fluid can be passed through said cell culture chamber while said tubular members and blade means are being rotated.

2. The bio-reactor as set forth in claim 1 wherein said blade means includes two lengthwise extending, equiangularly spaced blade members disposed about said central axis.

3. The bio-reactor as set forth in claim 1 wherein said second means includes a second shaft member coupled to said second tubular member, said third means includes a third shaft member coupled to said blade means and said first means includes bearing members rotatably mounted on said second and third shaft members.

4. The bio-reactor as set forth in claim 3 wherein said second means and said third means includes stationary bearing members for rotatably supporting said second and third shaft members.

5. The bio-reactors set forth in claim 1 wherein said first passage means includes a passage connected to peripheral openings disposed about said central axis for inputting fluid at each end of said culture vessel.

6. The bio-reactor as set forth in claim 5 wherein a radially outward annular surface at each end of said culture vessel is curved for guiding flow of fluid in the culture vessel.

7. The bio-reactor as set forth in claim 1 and further including sampling means in the wall of said cell culture vessel for retrieving a sample, said sampling means including a bore having a first opening to the interior of the cell culture vessel and a selectively operable valve member for opening and closing said first opening; a closed sampling second orifice passage intersecting said first orifice passage whereby a fluid sample can be extracted from said second passage when said first opening is opened.

8. The bio-reactor as set forth in claim 7, wherein said valve member has a portion which projects into the culture vessel through said first opening.

9. The bio-reactor as set forth in claim 1 and further including means for defining a closed loop fluid system for inputting fluid medium into said cell culture vessel and for outputting fluid medium through said second tubular member for recirculating said fluid medium.

10. The apparatus as set forth in claim 9 and further including means for adding constituent materials and liquids into the closed loop fluid system.

11. The bio-reactor system as set forth in claim 1 wherein said central second tubular member has a filter member for passing fluid, yet retaining cell cultures in said vessel.

12. The bio-reactor system as set forth in claim 11 and further including a heater means disposed about said first tubular member for heating said vessel.

13. The bio-reactor as set forth in claim 11 wherein said central second tubular member has inner and outer tubular portions and perforations disposed along the length of said tubular portions.

14. A bio-reactor system including a coaxially disposed elongated central tubular member, and tubular housing which define an elongated annular cell culture vessel;
    means for rotating said central tubular member and said tubular housing independently of one another about a common horizontally extending, longitude central, rotational axis and for simultaneously rotating a fluid medium and discrete suspension materials with a different density in the culture vessel and for placing such suspension materials in discrete spatial locations out of interference with one another in the culture vessel,
    means for inputting fresh nutrient fluid medium to the culture vessel and filter means for outputting spent fluid medium from the culture vessel through the central rotating tubular member while maintaining zero volume headspace in the culture vessel and while rotating said central tubular member and said tubular housing.

15. The apparatus as set forth in claim 14 and further including:
    elongated blade members circumferentially disposed about said rotational axis; and means for rotating said blade members about said rotational axis independently of said tubular member and said tubular housing.

16. The apparatus as set forth in claim 15 and further including:
selectively operable sampling means in said tubular housing for extracting a fluid sample including a first closed sample passageway which is accessible by sterile extractor means; and
a selectively actuated valve member for closing and opening the access of said passageway to the interior of said culture vessel.

* * * * *